(12) United States Patent
Song

(10) Patent No.: US 10,806,736 B2
(45) Date of Patent: Oct. 20, 2020

(54) **METHOD FOR PREVENTING OR TREATING TUBERCULOSIS BY A P53 EXPRESSION REGULATING COMPOSITION FOR *M. TUBERCULOSIS* CONTROL IN CELLS AND THE USE THEREOF**

(71) Applicant: THE INDUSTRY & ACADEMIC COOPERATION IN CHUNGNAM NATIONAL UNIVERSITY, Daejeon (KR)

(72) Inventor: Chang-Hwa Song, Daejeon (KR)

(73) Assignee: THE INDUSTRY & ACADEMIC COOPERATION IN CHUNGNAM NATIONAL UNIVERSITY, Daejeon (KR)

(*) Notice: Subject to any disclaimer, the term of this patent is extended or adjusted under 35 U.S.C. 154(b) by 0 days.

(21) Appl. No.: 16/392,446

(22) Filed: Apr. 23, 2019

(65) Prior Publication Data

US 2019/0321368 A1    Oct. 24, 2019

(30) Foreign Application Priority Data

Apr. 23, 2018  (KR) .................. 10-2018-0046757

(51) Int. Cl.
| | | |
|---|---|---|
| *A61K 31/519* | (2006.01) | |
| *A61K 45/06* | (2006.01) | |
| *A61P 31/06* | (2006.01) | |

(52) U.S. Cl.
CPC ............ *A61K 31/519* (2013.01); *A61K 45/06* (2013.01); *A61P 31/06* (2018.01)

(58) Field of Classification Search
USPC ........................................ 514/254
See application file for complete search history.

(56) References Cited

FOREIGN PATENT DOCUMENTS

| KR | 20080072894 A | 8/2008 |
|---|---|---|
| KR | 20120012297 A | 2/2012 |
| KR | 20130091061 A | 8/2013 |
| KR | 20160136450 A | 11/2016 |
| KR | 20170012559 A | 2/2017 |

*Primary Examiner* — Kathrien A Cruz

(57) ABSTRACT

The present invention relates to a pharmaceutical composition for preventing or treating tuberculosis comprising compound (K279-1558) as an active ingredient. Compound (K279-1558) which is an active ingredient of the present invention has an effect of inhibiting the proliferation of *M. tuberculosis* by inducing apoptosis of macrophages infected with tuberculosis through the overexpression of p53. Therefore, the method of the present invention comprising said compound as an active ingredient could be usefully used for preventing or treating tuberculosis.

6 Claims, 2 Drawing Sheets

[Fig. 1]
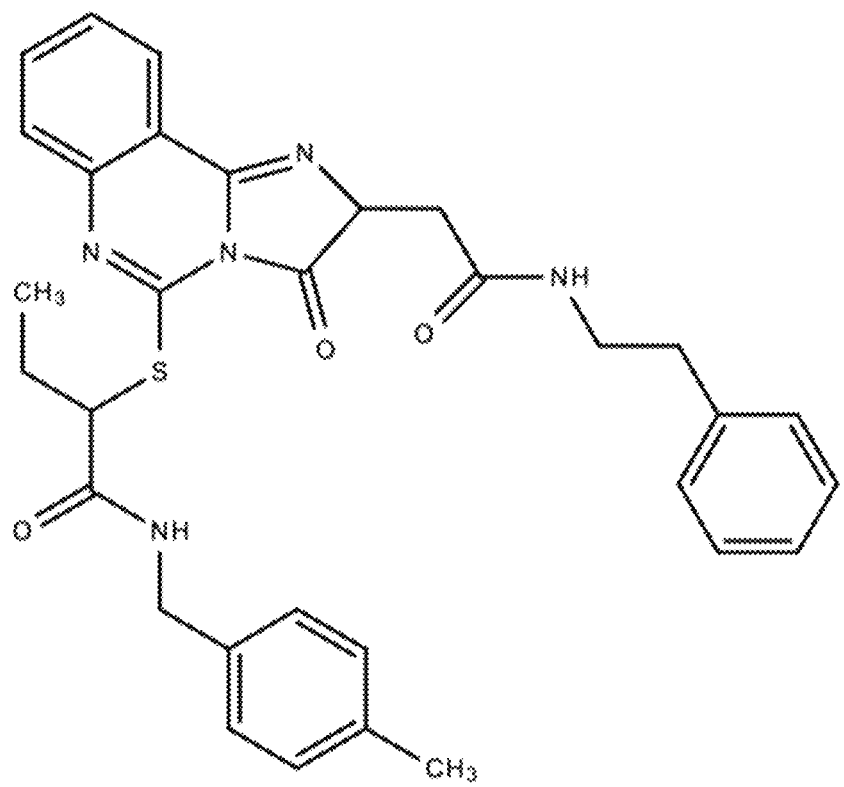
[Fig. 2]
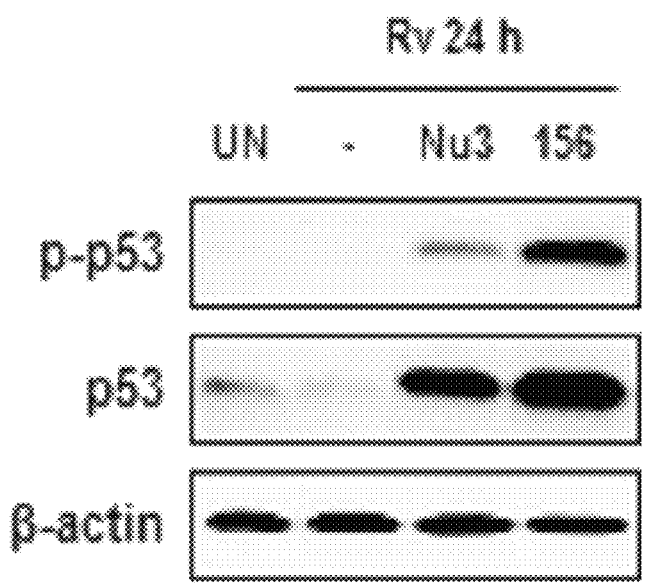

[Fig. 3]
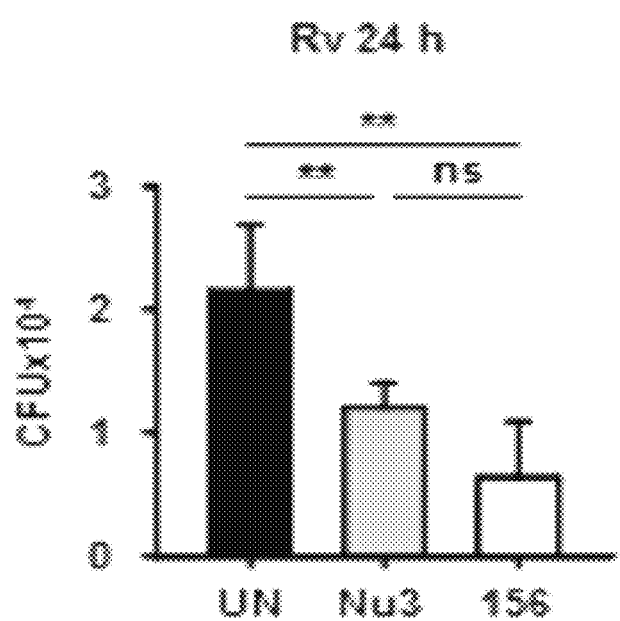

METHOD FOR PREVENTING OR TREATING TUBERCULOSIS BY A P53 EXPRESSION REGULATING COMPOSITION FOR *M. TUBERCULOSIS* CONTROL IN CELLS AND THE USE THEREOF

TECHNICAL FIELD

The present invention relates generally to the field of immunology. Specifically, the present invention relates to a method for preventing or treating tuberculosis by using a pharmaceutical composition comprising a p53 expression regulating composition as an active ingredient in order to inhibit the survival and proliferation of *M. tuberculosis*.

BACKGROUND ART

Tuberculosis is a chronic infectious disease caused by infection with *M. tuberculosis* and other *Mycobacterium* species. Tuberculosis is a major disease in developing countries causing 3 million deaths every year, and it is also an increasing problem in developed countries. About 8 million people are newly infected with tuberculosis every year.

Although tuberculosis infection may be asymptomatic for a considerable period of time, the disease is most commonly manifested as an acute inflammation of the lungs, resulting in fever and a nonproductive cough. If untreated, tuberculosis may result in serious complications and even death in the end.

Although tuberculosis may be treated using extended antibiotic therapy, such treatment is not sufficient to prevent the spread of tuberculosis. The infected individuals may be asymptomatic, but contagious, for some time. In addition, although compliance with the treatment regimen is critical, it would be difficult to monitor the patient's behavior. Some patients do not complete the course of treatment, which may lead to ineffective treatment and the development of drug resistance. Also, even if a full course of treatment is completed, infection with *M. tuberculosis* is not eradicated from the infected individual but remains as a latent infection which may still be reactivated. Therefore, tuberculosis is an infectious disease where it is very difficult to control the spread of the disease.

In order to control the spread of tuberculosis, effective vaccination and accurate early diagnosis are of utmost importance. Currently, vaccination with live bacteria is the most efficient method for inducing protective immunity. The most common *mycobacterium* used for this purpose is Bacillus Calmette-Guerin (BCG), which is an avirulent strain of *M. bovis*. However, the safety and efficacy of BCG is a source of controversy, and some countries such as the U.S. do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48 to 72 hours after injection, which indicates exposure to mycobacterial antigens. However, sensitivity and specificity have been a problem with this test, and individuals vaccinated with BCG cannot be distinguished from infected individuals.

Meanwhile, p53 (molecular weight 53 kDa) is a representative anticancer gene which has the function of inhibiting cell hyperplasia and mutation. Also, as a transcription factor, p53 is a protein effective in inducing the death of cancer cells and cells infected with bacteria by increasing the expression of PUMA, Bax, etc. associated with apoptosis. Therefore, it is deemed that p53 would play an important role in killing *M. tuberculosis* of macrophages.

P53 protein is ubiquitinated by MDM2 protein and dissolved by proteasome. Nutlin-3α (molecular weight 581.49), which is known as an anticancer drug, is a compound which binds to MDM2 to inhibit p53-MDM2 interaction, thereby increasing the p53 pathway activity. Therefore, there is a need to develop a composition which could be used alone or in combination with the existing anti-tuberculosis drugs as a method for inhibiting *M. tuberculosis* targeting at p53.

PRIOR ART DOCUMENT

Patent Document (Patent document 1) Korean Patent Laid-Open No. 10-2012-0012297

SUMMARY OF INVENTION

Task to be Solved

The present invention aims at contributing to the activation of macrophages using a p53 expression regulating compound or a p53 activity inducing compound (K279-1558), thereby providing a method for preventing or effectively treating tuberculosis which has an action mechanism different from the existing drugs and has relatively fewer side effects.

Means for Solving the Task

In order to achieve the above object, the present invention aims at providing a pharmaceutical composition for preventing or treating tuberculosis which comprises a p53 activity inducing compound (K279-1558) as an active ingredient.

The compound provided as above is characterized by overexpressing p53. The p53 overexpression is characterized by inhibiting the proliferation of *M. tuberculosis* by inducing apoptosis of macrophages infected with *M. tuberculosis*.

An existing anti-tuberculosis drug may be used together with the p53 activity inducing compound (K279-1558). The anti-tuberculosis drug used here may be at least one selected from a group consisting of rifampicin, isoniazid, ethambutol and pyrazinamide.

The tuberculosis may be at least one selected from a group consisting of eye tuberculosis, skin tuberculosis, adrenal tuberculosis, renal tuberculosis, epididymal tuberculosis, lymphatic gland tuberculosis, laryngeal tuberculosis, middle ear tuberculosis, intestinal tuberculosis, multidrug-resistant tuberculosis, pulmonary tuberculosis, sputum tuberculosis, bone tuberculosis, throat tuberculosis, lymphatic tuberculosis, lung deficiency, breast tuberculosis and spinal tuberculosis.

Effect of Invention

According to the present invention, since a pharmaceutical composition which comprises a compound whose function has not been known before as an active ingredient is used, it could be expected to have an effect of preventing and treating *M. tuberculosis* which has multiple drug resistance against existing drugs. Also, according to the present invention, since it would be possible to inhibit the growth of cells with latent *M. tuberculosis* infection, it would be possible to remove latent *M. tuberculosis* in case of using the compound alone or together with existing drugs.

BRIEF DESCRIPTION OF DRAWINGS

FIG. 1 is a photograph showing the formula of the compound (K279-1558) of the present invention;

FIG. 2 is an electrophoresis photograph of protein expression by western blotting showing p53 activity by subjecting macrophages infected with *M. tuberculosis* to Nutlin-3α and the compound (K279-1558) of the present invention; and FIG. 3 is a graph showing the sharp decrease in the number of *M. tuberculosis* in macrophages by subjecting macrophages to Nutlin-3α and the compound (K279-1558) of the present invention.

DETAILS MEANS FOR CARRYING OUT THE INVENTION

Hereinafter, the present invention will be explained in more detail with reference to the attached drawings. However, the attached drawings are merely examples for easily explaining the contents and scope of the technical idea of the present invention, and the technical scope of the present invention shall not be limited or modified by them. Also, it would be obvious to a person skilled in the art that various modifications and alternations could be made within the scope of the technical idea of the present invention based on the examples.

The present invention revealed for the first time that the compound of the following formula 1 (K279-1558) shows a remarkably higher p53 expression than Nutlin-3α, which activates the apoptosis of macrophages, and thus is effective in preventing or treating *M. tuberculosis*. Accordingly, the present invention is characterized by providing a composition for preventing or treating *M. tuberculosis* comprising the compound of the following formula 1 (no. 156) as an active ingredient.

[Formula 1]

'Nutlin-3α' is an anti-cancer drug currently under clinical development for the treatment of solid cancer, etc. Specifically, MDM2 protein binds to the transactivation site of p53, which is known as a gene for inhibiting cancer, and plays the role of blocking the activity thereof. In this regard, the Nutlin-3α compound binds to MDM2 protein to inhibit p53-MDM2 interaction. Nutlin-3α has a molecular structure similar to that of p53, and thus binds to MDM2 protein, allowing p53 protein not to bind to MDM2 protein and maintain p53 activity, thereby allowing p53 overexpression.

However, there has been no research on the compound of the present invention (K279-1558), and thus the detailed functions thereof have not been revealed. Also, it has not been reported that the compound has an effect against various diseases including the treatment of tuberculosis. In this regard, the present inventors completed the present invention by confirming that the compound of the present invention (K279-1558) of formula 1 has an effect of improving tuberculosis through a mechanism activating p53.

According to the following example 1, in case of subjecting the compound of the present invention (K279-1558) to bone marrow-derived macrophages (BMDMs), which is a rat-derived macrophage, it could be confirmed that the number of *M. tuberculosis* dropped sharply. Accordingly, the Nutlin-3α compound has an effect of improving tuberculosis, and thus the composition of the present invention comprising the compound as an active ingredient may be usefully used for preventing or treating tuberculosis.

Tuberculosis mentioned in the present invention may include eye tuberculosis, skin tuberculosis, adrenal tuberculosis, renal tuberculosis, epididymal tuberculosis, lymphatic gland tuberculosis, laryngeal tuberculosis, middle ear tuberculosis, intestinal tuberculosis, multidrug-resistant tuberculosis, pulmonary tuberculosis, sputum tuberculosis, bone tuberculosis, throat tuberculosis, lymphatic tuberculosis, lung deficiency, breast tuberculosis, or spinal tuberculosis, etc.

As used herein, unless otherwise indicated, the term "treating" means reversing, alleviating, inhibiting the progress of, or preventing a disorder or a disease to which the term applies, or one or more symptoms of such disorder or the disease. The term "treatment," as used herein, refers to the act of treating as "treating" is defined as above.

Also, said treatment means an act performed by administering the pharmaceutical composition of the present invention into an individual. The pharmaceutical composition of the present invention may be formulated into various forms including oral formulations such as a powder, a granule, a tablet, a suspension, an emulsion, a syrup, an aerosol, etc., an external formulation, a suppository, and a sterilized injectable solution, and then may be administered. The pharmaceutical composition of the present invention may be administered through various paths into mammals such as rats, mice, livestock, human, etc.

Hereinafter, the present invention will be described in more detail through detailed examples.

Example 1: Effect of Inhibiting the Growth of *M. tuberculosis* in Cells by Regulating p53 Expression It is confirmed whether p53 is expressed, when a cell is infected with *M. tuberculosis*, by subjecting the cell to the compound (K279-1558). Also, in order to analyze the role of p53 expression, the effect of p53 expression is confirmed from macrophages infected with *M. tuberculosis*. The cells were infected with avirulent *M. tuberculosis* (*Mycobacterium tuberculosis* H37Ra) in a ratio of one bacterium per cell by using bone marrow-derived macrophages (BMDMs), which is a rat-derived macrophage, and then the cells were subjected to Nutlin-3α and the compound (K279-1558) in a concentration of 10 μM. Thereafter, the number of *M. tuberculosis* surviving in the cells was measured.

FIG. 2 shows the result confirming the degree of p53 protein expression expressed when infected with *M. tuberculosis* by western blotting. The result shows that p53 activity increases remarkably when the macrophages infected with *M. tuberculosis* is subjected to the compound of formula 1 (K279-1558) (FIG. 1), as compared to the case where the macrophages infected with *M. tuberculosis* is subjected to Nutlin-3α which is known as a p53 (in FIG. 2, β-actin is the inner control).

In FIG. 3, a macrophage infected with *M. tuberculosis* is subjected to Nutlin-3α and the compound of formula 1 (K279-1558) in a concentration of 10 μM, and the number of *M. tuberculosis* surviving in the cell after 24 hours was calculating by cultivating in a 7H10 agar medium for 14 to 21 days. As a result, it can be seen that the number of avirulent *M. tuberculosis* surviving in macrophages subjected to Nutlin-3α and the compound (K279-1558) decreased sharply, as compared to the control group. The method used for statistical processing is the Bonferroni's multiple comparison test. The result is indicated as * when the p-value is below 0.05, the result is indicated as  when the p-value is less than 0.01, and the result is indicated as * when the p-value is less than 0.001.

What is claimed is:

1. A method for treating tuberculosis by administering into an individual a pharmaceutical composition comprising the compound of the following formula 1 as an active ingredient:

[Formula 1]

2. The method of claim 1, wherein the compound of formula 1 overexpresses p53.

3. The method of claim 2, wherein the p53 overexpression inhibits the proliferation of *M. tuberculosis* by inducing apoptosis of macrophages infected with *M. tuberculosis*.

4. The method of claim 1, wherein an anti-tuberculosis drug is used together with the compound of formula 1.

5. The method of claim 4, wherein the anti-tuberculosis drug is rifampicin, isoniazid, ethambutol or pyrazinamide.

6. The method of any one of claim 1, wherein the tuberculosis is eye tuberculosis, skin tuberculosis, adrenal tuberculosis, renal tuberculosis, epididymal tuberculosis, lymphatic gland tuberculosis, laryngeal tuberculosis, middle ear tuberculosis, intestinal tuberculosis, multidrug-resistant tuberculosis, pulmonary tuberculosis, sputum tuberculosis, bone tuberculosis, throat tuberculosis, lymphatic tuberculosis, breast tuberculosis, or spinal tuberculosis.

* * * * *